(12) United States Patent
Yu et al.

(10) Patent No.: US 10,082,017 B2
(45) Date of Patent: Sep. 25, 2018

(54) SYSTEM AND METHOD FOR A BONDED DIFFERENTIAL MAGNETIC SENSOR ARRAY USING PULSED EDDY CURRENT FOR CASED-HOLE APPLICATIONS

(71) Applicant: GOWell International, LLC, Houston, TX (US)

(72) Inventors: Yanxiang Yu, Houston, TX (US); Jinsong Zhao, Houston, TX (US)

(73) Assignee: GOWell International, LLC, Houston, TX (US)

( * ) Notice: Subject to any disclaimer, the term of this patent is extended or adjusted under 35 U.S.C. 154(b) by 180 days.

(21) Appl. No.: 14/857,570

(22) Filed: Sep. 17, 2015

(65) Prior Publication Data

US 2017/0081955 A1    Mar. 23, 2017

(51) Int. Cl.
*G01V 3/10* (2006.01)
*G01V 3/18* (2006.01)
*E21B 47/12* (2012.01)
*G01N 27/90* (2006.01)
*G01V 3/28* (2006.01)

(52) U.S. Cl.
CPC ......... *E21B 47/12* (2013.01); *G01N 27/9033* (2013.01); *G01V 3/28* (2013.01)

(58) Field of Classification Search
CPC ....... E21B 47/12; G01N 27/9033; G01V 3/28
USPC .................................................. 324/346, 339
See application file for complete search history.

(56) References Cited

U.S. PATENT DOCUMENTS

| 7,960,969 B2 * | 6/2011 | Mouget | G01V 3/28 324/221 |
| 2014/0097848 A1 * | 4/2014 | LeBlanc | E21B 47/06 324/338 |

* cited by examiner

*Primary Examiner* — Reena Aurora

(57) ABSTRACT

A system and method for inspecting a tube comprising a telemetry module, a centralizing module, an inspection device, a differential amplifier, a sensor array, and a service device. In embodiments, a tube inspection device may comprise a sensor array. The sensor array may further comprise a center receiver coil, a ferri-core, a peripheral receiver, and a transmitter coil. A method for inspection a tube may comprise inserting an inspection device into a tube, energizing a sensory array, inducing an eddy current within the tubing, and measuring voltage with a center receiver coil and a peripheral receiver of the sensor array.

4 Claims, 12 Drawing Sheets

SYSTEM AND METHOD FOR A BONDED DIFFERENTIAL MAGNETIC SENSOR ARRAY USING PULSED EDDY CURRENT FOR CASED-HOLE APPLICATIONS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Field of the Invention

This invention relates to a field for imaging wall thickness variations, changes in tubing, imaging casing through a tube, and imaging multiple tubes using non-destrctive means in cased-hole downhole logging applications. The changes and variations of tubing walls may be caused by internal and/or external patches, clamps, corrosions, errosions, and/or any combination thereof.

Background of the Invention

Tubing may be used in many different applications and may transport many types of fluids. Many times tubes may be placed underground and/or positioned in an inaccessible area, making inspection of changes within tubing difficult. It may be beneficial to measure the thickness variations within a tube while the tube is in use. Previous methods for inspecting tubes have come in the form of non-destructive inspection tools such as electromagnetic devices that may measure magnetic flux-leakage within tubing, which may not be able to detect changes in multi-pipe situations. Additionally, previous methods may not be able to perform multi-pipe azimuthal imaging. Electromagnetic devices may be well suited for tube inspection because they may operate and be insensitive to any fluid within the tube.

Previous devices and methods that may measure flux-leakage may only be useful for the detection of localized damage in ferromagnetic pipes. The measurement of flux-leakage may be hindered by the type of tube, thinning of tubing, requirements of a strong magnetic field, strong flux coupling, and a requirement for the device to be in close proximity to the tube walls. Additionally, electromagnetic tools that use eddy-current may be better suited for measuring the integrity of tubing. Drawbacks of a constant eddy-current electromagnetic tool may be that the signal from several frequencies may not penetrate a first wall of tubing and allow inspection of the integrity of a second wall of a larger surrounding tubing. Transient electromagnetic methods using pulsed electromagnetic waves may be limited to increasing the signals from a second tube wall to additional tube walls, have problems optimizing a receiver coil, and may suffer Signal-to-Noise Ratio problems.

Consequently, there is a need for an electromagnetic tool which may induce a larger amount of eddy-current within surrounding pipe walls. In downhole applications, multi-piping wall variation imaging detection capability may be in high demand. Demands may include locating clamps of permanent waveguide production monitering wells for muti-perforations, through-tubing casing deformation measurement, tube eccentricity within casing, and imaging of corrosions for multiple pipes.

BRIEF SUMMARY OF SOME OF THE PREFERRED EMBODIMENTS

These and other needs in the art may be addressed in embodiments by a system and method for inspecting a tube. A tube inspection system may comprise a telemetry module, in which the telemetry module comprises an accelerometer. In embodiments the tube inspection system may comprise a centralizing module, in which the centralizing module may comprise at least three arms and an inspection device. The inspection device may comprise a memory module, a differential amplifier, and a sensor array. The sensor array may comprise a center receiver coil, a ferri-core, a peripheral receiver, and a transmitter coil. Additionally, the tube inspection system may comprise a service device.

In embodiments, an inspection device may comprise a sensor array, in which the sensor array may comprise a center receiver coil, a ferri-core, a peripheral receiver, and a transmitter coil. The peripheral receiver may be wound around a portion of the ferri-core, in which the ferric-core may be attached to the center receiver. The transmitter coil may be wound around a portion of the ferri-core.

A method for inspecting a tube may comprising inserting an inspection device into a tube, in which the inspection device may comprise a sensory array, a differential amplifier, and a memory unit. The method may further comprise energizing the sensory array, in which an electro-magnetic field may be emitted from the sensor array. Further inducing an eddy current within the tubing and measuring voltage with a center receiver coil and a peripheral receiver of the sensor array.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

The present disclosure relates to embodiments of a device and method for inspecting and detecting characteristics of tubing and devices attached to tubing. More particularly, embodiments of a device and method are disclosed for inspecting a number of tube walls surrounding an innermost tube wall. In embodiments, an inspection device may induce an eddy current in surrounding tube walls by producing an electro-magnetic field, wherein the induced eddy current may be recorded and analyzed for aberrations. Eddy currents may be produced by a bonded sensor array, which may be switched on and off to produce and record an induced eddy current in a tube and/or surrounding tube walls. The eddy current decay and diffusion in the tube walls may be recorded, specifically recording voltage in embodiments, which may produce a function of the tube thickness and electromagnetic properties (e.g. metal conductivity and magnetic permeability) and the configurations of tubes. In embodiments, the power provided to different sensors may be the same and/or different. Manipulation of the configuration of ferri-cores may manipulate the transmission and direction of the electro-magnetic field.

In embodiments, an inspection device may be a bonded differential magnetic sensor array. The inspection device may boost the electro-magnetic field outside tubing by creating an orthogonal, or substantially orthogonal, magnetic field within the tubing, which may provide a higher accuracy in outside tube thickness measurement. In embodiments, the electro-magnetic field may be a focused perpendicular to the incident of inspected tubing. The inspection device may be used to measure tubing thickness, aberrations in tubing, and/or devices attached to the tubing.

Figure 1:
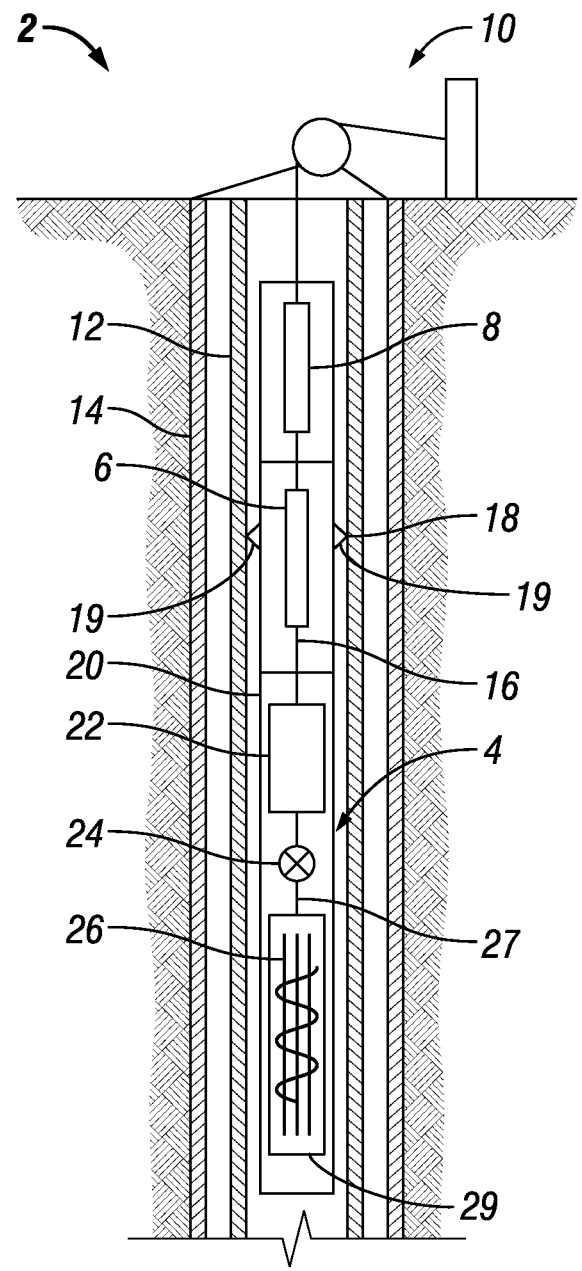
FIG. 1 illustrates an embodiment of an inspection system disposed downhole.

FIG. 1 illustrates an inspection system 2 comprising an inspection device 4, a centralizing module 6, a telemetry module 8, and a service device 10. In embodiments, inspection device 4 may be inserted into tubing 12, wherein tubing 12 may be contained within casing 14. In further embodiments, not illustrated, there may be a plurality of tubing 12, wherein an inner tube may be contained by several additional tubes. In embodiments, as shown, inspection device 4 may be disposed below centralizing module 6 and telemetry module 8. In other embodiments, not illustrated, inspection device 4 may be disposed above and/or between centralizing module 6 and telemetry module 8. In embodiments, inspection device 4, centralizing module 6, and telemetry module 8 may be connected to tether 16. Tether 16 may be any suitable cable that may support inspection device 4, centralizing module 6, and telemetry module 8. A suitable cable may be steel wire, steel chain, braided wire, metal conduit, plastic conduit, ceramic conduit, and/or the like. A communication line, not illustrated, may be disposed within tether 16 and connect inspection device 4, centralizing module 6, and telemetry module 8 with service device 10. Without limitation, inspection system 2 may allow operators on the surface to review recorded data in real time from inspection device 4, centralizing module 6, and telemetry module 8.

As illustrated in FIG. 1, service device 10 may comprise a mobile platform (i.e. a truck) or stationary platform (i.e. a rig), which may be used to lower and raise inspection system 2. In embodiments, service device 10 may be attached to inspection system 2 by tether 16. Service device 10 may comprise any suitable equipment which may lower and/or raise inspection system 2 at a set or variable speed, which may be chosen by an operator. The movement of inspection system 2 may be monitored and recorded by telemetry module 8.

Telemetry module 8, as illustrated in FIG. 1, may comprise any devices and processes for making, collecting, and/or transmitting measurements. For instance, telemetry module 8 may comprise an accelerator, gyro, and the like. In embodiments, telemetry module 8 may operate to indicate where inspection system 2 may be disposed within tubing 12 and the orientation of sensor array 26. Telemetry module 8 may be disposed at any location above, below, and/or between centralizing module 6 and inspection device 4. In embodiments, telemetry module 8 may send information through the communication line in tether 16 to a remote location such as a receiver or an operator in real time, which may allow an operator to know where inspection system 2 may be located within tubing 12. In embodiments, telemetry module 8 may be centered laterally in tubing 12.

As illustrated in FIG. 1, centralizing module 6 may be used to position inspection device 4 and/or telemetry module 8 inside tubing 12. In embodiments, centralizing module 6 laterally positions inspection device 6 and/or telemetry module 8 at about a center of tubing 12. Centralizing module 6 may be disposed at any location above and/or below telemetry module 8 and/or inspection device 4. In embodiments, inspection centralizing module 6 may be disposed above inspection device 4 and below telemetry module 8. Centralizing module 6 may comprise arms 18. In embodiments, there may be a plurality of arms 18 that may be disposed at any location along the exterior of centralizing module 6. Specifically, arms 18 may be disposed on the exterior of centralizing module 8. In an embodiment, as shown, at least one arm 18 may be disposed on opposing lateral sides of centralizing module 6. Additionally, there may be at least three arms 18 disposed on the outside of centralizing module 6. Arms 18 may be moveable at about the connection with centralizing module 6, which may allow the body of arm 18 to be move closer and farther away from centralizing module 6. Arms 18 may comprise any suitable material. Suitable material may be but is not limited to, stainless steel, titanium, metal, plastic, rubber, neoprene, and/or any combination thereof. In embodiments, the addition of springs 19 may further make up and/or be incorporated into centralizing module 6. Springs 19 may assist arms 18 in moving centralizing module 6 away from tubing 12, and thus inspection device 4 and telemetry module 8, to about the center of tubing 12. Without limitation, centering inspection device 2 may produce more reliable and accurate voltage readings of tubing 12.

Inspection device 4, as illustrated in FIG. 1, may be located below centralizing module 6 and/or telemetry module 8. Inspection device 4 may be designed to detect defects and measure wall thickness in tubing 12 and surrounding tubing. In embodiments, inspection device 4 may be able to detect, locate transverse and longitudinal defects (both internal and external), determine the deviation of the wall thickness from its nominal value thorough the interpretation of voltage data. Tubing 12 may be made of any suitable material for use in a wellbore. Suitable material may be, but is not limited to, metal, plastic, and/or any combination thereof. Additionally, any type of fluid may be contained within tubing 12 such as without limitation, water, hydrocarbons, and the like. In embodiments, there may be additional tubing which may encompass tube 12. Inspection device 4 may comprise a housing 20, a memory module 22, a differential amplifier 24, and a sensory array 26. Housing 6 may be any suitable length in which to protect and house the components of inspection device 4. In embodiments, housing 20 may be made of any suitable material to resist corrosion and/or deterioration from a fluid. Suitable material may be, but is not limited to, titanium, stainless steel, plastic, and/or any combination thereof. Housing 20 may be any suitable length in which to properly house the components of inspection device 4. A suitable length may be about one foot to about ten feet, about four feet to about eight feet, about five feet to about eight feet, or about three feet to about six feet. Additionally, housing 20 may have any suitable width. A suitable diameter may be about one foot to about three feet. about one inch to about three inches, about three inches to about six inches, about four inches to about eight inches, about six inches to about one foot, or about six inches to about two feet. Housing 20 may protect memory module 22, differential amplifier 24, and sensory array 26 from the surrounding downhole environment within tubing 12.

As illustrated in FIG. 1, memory module 22 may be disposed within inspection device 4. In embodiments, memory module 22 may store all received recorded and measured data and may transmit the data in real time through a communication line in tether 16 to a remote location such as an operator on the surface. Memory module 22 may comprise flash chips and/or ram chips which may be used to store data and/or buffer data communication. Additionally, memory module 22 may further comprise a transmitter, processing unit and/or a microcontroller. In embodiments, memory module 22 may be removed from inspection device 4 for further processing. Memory module 22 may be disposed within any suitable location of housing 20. Such as, about the top, about the bottom, or about the center of housing 20. In embodiments, memory module 22 may be in communication with differential amplifier 24 and sensor array 26 by any suitable means such as by a connection to differential amplifier 24 and sensor array 26 by a communication line 27. Memory module 22 may record voltage recordings transmitted from differential amplifier 24.

Differential amplifier 24, as illustrated in FIG. 1, may be an electronic amplifier that may amplify the differences between two input voltages but may suppress any voltage that may be common in the two inputs. Additionally, differential amplifier 24 may help boost and filter voltage signals recorded by sensor array 26. In embodiments, differential amplifier 24 may filter each and every recorded voltage from sensor array 26. This may allow inspection device 4 to record and illustrate the differences between recorded voltages in a graphical representation. Differential amplifier 24 may be disposed at any suitable location within housing 20. In embodiments, such disposition may be about the top, about the bottom, or about the center of housing 20. In embodiments, boosted and filtered voltages from differential amplifier 24 may help in the identification of the change in magnetic field characteristics transmitted from sensory array 26 as sensor array 26 moves through tubing 12.

Figure 2:
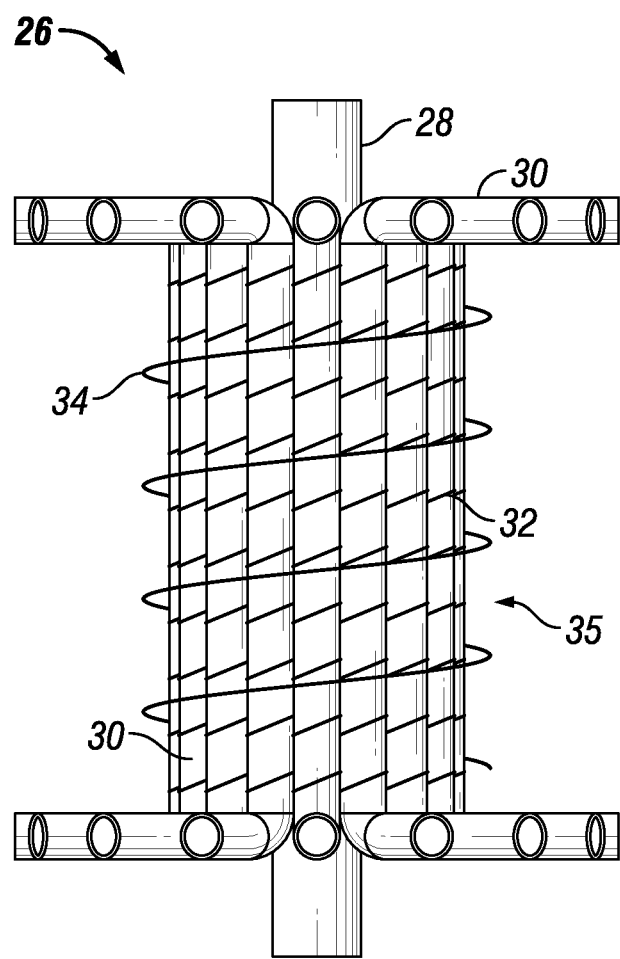
FIG. 2 illustrates an embodiment of a sensor array.

As illustrated in FIGS. 1 and 2, sensor array 26 may create an electro-magnetic field, which may induce an eddy current in surrounding tubing 12. The voltage charge within tubing 12, from the induced eddy current, may be sensed and recorded by sensor array 26. In embodiments, the recorded voltage may allow identification of the characteristics of tubing 12, discussed below. Sensor array 26 may be disposed within a sensor array housing 29. Sensor array housing 29 may be composed of any suitable non-ferrous material such as plastic, ceramic, and the like. In embodiments, sensor array 26 may be disposed in a fluid within sensor array housing 29. This may prevent sensor array 26 from moving during operations and further protect sensor array 26 from subsurface pressure. Sensor array 26 may be disposed at any suitable location within housing 20. Such disposing may be at about the top, about the bottom, or about the center of housing 20. Additionally, there may be a plurality of sensor arrays 26 disposed throughout housing 20. As illustrated in FIG. 2, sensory array 26 may comprise at least one center receiver coil 28, at least one ferri-core 30, at least one peripheral receiver 32, and at least one transmitter coil 34. In embodiments, center receiver coil 28 may comprise any suitable material. Suitable material may be, but is not limited to, aluminum, copper, nickel, steel, and/or any combination thereof. Center receiver coil 28 may be any suitable length. A suitable length may be, but is not limited to, about one inch to about three inches, about two inches to about four inches, about three inches to about six inches, about four inches to about eight inches, about five inches to about ten inches, or about six inches to about twelve inches. Center receiver coil 28 may be longer than ferri-core 30. Center receiver coil 28 may be any suitable shape. A suitable shape may be, but is not limited to, round, oval, square, triangular, polyhedral, and/or any combination thereof. In embodiments, center receiver coil 28 may provide a structure in which ferri-core 30, peripheral receiver 32, and transmitter coil 34 may be disposed. Center receiver coil 28 may sense voltage from the emitted electro-magnetic field as originally transmitted by sensory array 26. This may serve as a base voltage that may be compared to voltages recorded by peripheral receivers 32. With a base measurement, the difference in the voltages measured from tubing 12 may be used to identify characteristics of tubing 12. The electro-magnetic field may be transmitted, directed, and focused within a desired area by ferri-core 30.

Figure 3A:
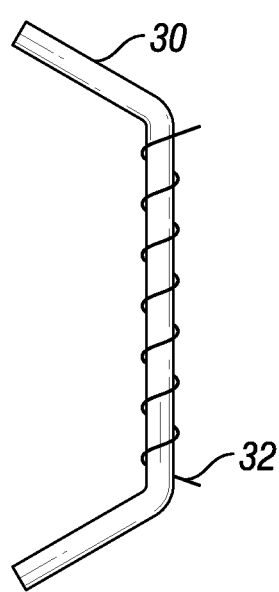
FIG. 3a illustrates an embodiment of a V shaped sensor.
Figure 3B:
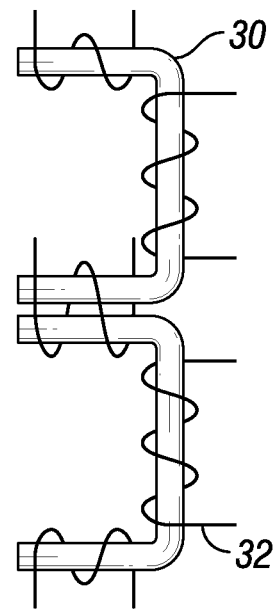
FIG. 3b illustrates an embodiment of a E shaped sensor.
Figure 3C:
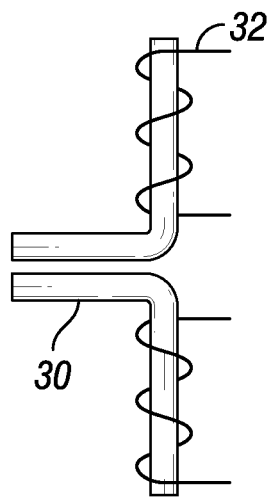
FIG. 3c illustrates an embodiment of a T shaped sensor.
Figure 3D:
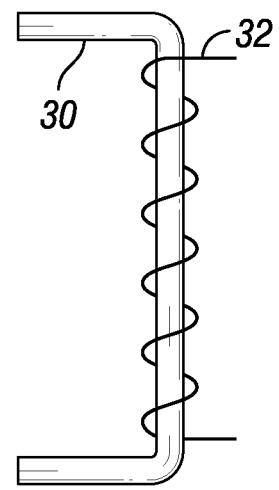
FIG. 3d illustrates an embodiment of a Pi shaped sensor.

Ferri-core 30, as illustrated in FIG. 2 may be used to produce an electro-magnetic field, which may induce an eddy current within tubing. 12. In embodiments, ferri-core 30 may comprise any suitable material. Suitable material may be, but is not limited to, ferrite, silicon steel, nickel steel, alloy powder core, and/or any combination thereof. Ferri-core 30 may be any suitable length. A suitable length may be, but is not limited to, about one inch to about three inches, about two inches to about four inches, about three inches to about six inches, about four inches to about eight inches, about five inches to about ten inches. or about six inches to about twelve inches. In embodiments, fern -core 30 may be shorter than center receiver coil 28. Ferri-core 30 may by any suitable shape. A suitable shape may be, but is not limited to, round, oval, square, triangular. polyhedral, and/or any combination thereof. Additionally, ferri-core 30 may be configured in any suitable structure in which to transmit an electro-magnetic field to and through tubing 12. As illustrated in FIGS. 3a-3d, structures of ferri-core 30 may vary. Specifically, a configuration may be V-shaped (FIG. 3a), E-shaped (FIG. 3b), T-shaped (FIG. 3c), and/or Pi-shaped (FIG. 3d). Each configuration may produce a different type of electro-magnetic field. For example, a V-shaped ferri-core 30 may focus the electro-magnetic field to a desired depth and may decrease the diameter of sensor array 26. An E-shaped ferri-core 30 may focus the electro-magnetic field in a center of an upper half plane and/or a bottom half plane. A T-shaped ferri-core 30 may generate a larger symmetrical electro-magnetic field. A Pi-shaped ferri-core 30 may generate and focus an electro-magnetic field that may be perpendicular to a tube, which may penetrate the tube. In embodiments, sensor array 26 may have a single structure configuration for each individual ferri-core 30. Additionally, sensor array 26 may have any number of combinations of structure configurations of ferri-core 30. In embodiments, referring to FIG. 2, ferri-core 30 may be disposed about a portion of the exterior of center receiver coil 28, where center receiver coil 28 extends through ferri-core 30. Ferri-core 30 may completely surround a portion of center receiver coil 28, which may create a three hundred and sixty degree electro-magnetic field. Additionally, a plurality of ferri-cores 30 may be disposed adjacent to the center receiver coil 28, which may form a ferri-core bundle 35. Ferri-core bundle 35 may comprise at least two ferri-cores 30. In embodiments, ferri-core bundle 35 may be held together by transmitter coil 34, described below. An electro-magnetic field may be produced when ferri-core 30 or a plurality of ferri-cores 30 are energized. In embodiments, a plurality of ferri-cores 30 may be energized individually, in distinct groups, or every ferri-core at once. Additionally, ferri-cores 30 may be energized simultaneously, at different rates, or at different times. The configuration of ferri-core 30 may direct the electro-magnetic field through a single tube 12 and into additional tubes, not illustrated. This may allow inspection device 4 to induce an eddy current in additional tubing that may surround tube 12. The voltage created by induced eddy current in the outer tubing may be recorded by peripheral receivers 32, which may determine characteristics of each individual tube 12.

As illustrated in FIG. 2, peripheral receivers 32 may be a wire, which may be wound around each ferri-core 30. In embodiments, peripheral receivers 32 may comprise any suitable material. Suitable material may be, but is not limited to, aluminum, copper, nickel, steel, and/or any combination thereof. Peripheral receivers 32 may be wound any number of times around ferri-core 30. Additionally, the number of peripheral receivers 32 may affect the azimuthal resolution of sensor array 26. Specifically, the greater number of peripheral receivers 32, the greater the azimuthal resolution. During operation, peripheral receivers 32 may record the voltage produced by inducing an eddy current within tubing 12. Additionally, center receiver 28 may eliminate the interferences between two peripheral receivers 32. In embodiments, peripheral receivers 32 may sense voltage induced in tubing 12, or additional tubing surrounding tubing 12.

Transmitter coil 34, as illustrated in FIG. 2 may be a wire, which may be wound around all ferri-cores 30 and center receiver coil 28. In embodiments, transmitter coil 34 may comprise any suitable material. Suitable material may be, but is not limited to, aluminum, copper, nickel, steel, and/or any combination thereof. In embodiments, transmitter coil 34 may eliminate coupling power between transmitter coil 34, center receiver coil 28, as well as peripheral coil 32. This may be accomplished as each ferri-core 30 may transmit magnetic flux with transmitter coil 34. The magnetic flux may be directed in the same direction due to each ferri-core 30, which may eliminate individual magnetic flux loops. Transmitter coil 34 may boost the power associated with the production of an electro-magnetic field. This may increase the distance in which the electro-magnetic field may extend from sensor array 26. During operation, transmitter coil 34 may be energized to produce an electro-magnetic field, which may induce an eddy current in tubing 12. Transmitter coil 34 may then be switched off, which may allow for center receiver coil 28 and peripheral receiver 32 to record the voltage within tubing 12, as produced from the induced eddy current. A microprocessor and/or control unit may be used to direct current into and out of transmitter coil 34. Current may be used to energize transmitter coil 34, which may create an electro-magnetic field. Additionally, the microprocessor may be used to record and transmit the recorded voltages within receiver coil 28.

Figure 4:
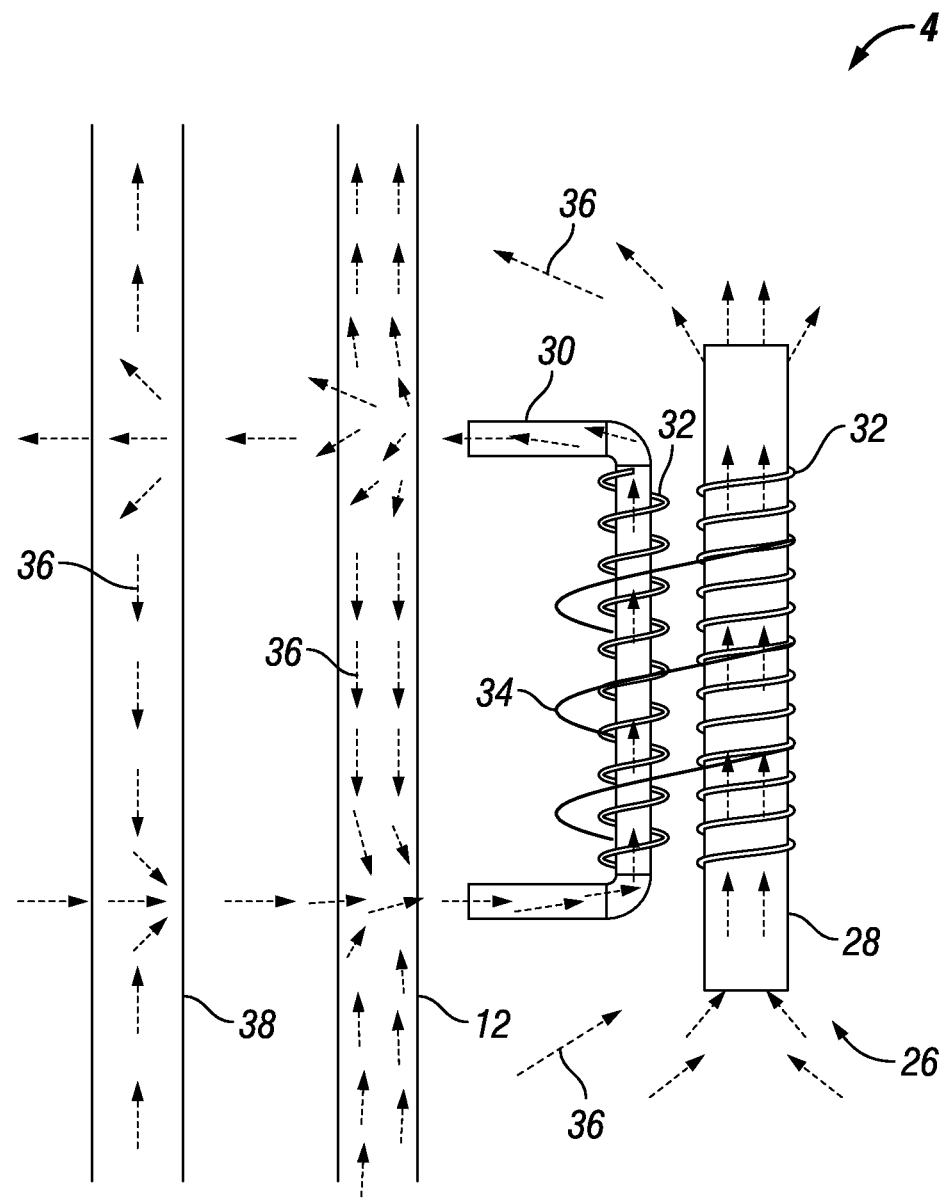
FIG. 4 illustrates an embodiment of a magnetic field produced by a sensor array.

As illustrated in FIG. 4, electro-magnetic field 36 may be produced and emitted from sensor array 26. In embodiments, electro-magnetic field 36 may be strong and large enough to induce an eddy current in second tube 38. It should be noted that electro-magnetic field 36 may induce an eddy current in additional outside tubing not illustrated. Electro-magnetic field 36 may be directed by ferri-core 30. As discussed above, different configurations of ferri-core 30 may direct electro-magnetic field 36 differently, which may be selected by the operator. In embodiments, transmitter coil 34 may be turned off and on at any given length of time. When turned on, the transmitter coil 34 may produce an electro-magnetic field 36, which may be directed by ferri-core 30 and induce eddy current in tubing 12. Transmitter coil 34 may then be switched off, which may allow for center receiver coil 28 and peripheral receivers 32 to sense and record the voltage produced by the induced eddy current. Turning transmitter coil 34 on and off may be repeated continuously as measurements of tube 12 are performed.

Measurements, inspections, and detection may take place as inspection device 4 moves through tube 12 in any direction. Travel time of inspection device 4 through a zone of interest within tube 12 may depend on the duration of pulses and amplitude used to produce and transmit an electro-magnetic field 36 through inspection device 4. Duration of a pulse may be set so that the signal variation between the excitation time and the "infinite" excitation time may be less than the noise constantly detected at signal level. Duration may vary based on the "electromagnetic" wall thickness of the inspected tube 12. Electromagnetic wall thickness refers to the given conductivity and relative permeability with tube 12 thickness. Transmitter coil 34 may generate an electro-magnetic field 36. The electro-magnetic field 36 created by the pulse may be used to induce an eddy current in tube 12 and/or additional tubing. Additionally, ferri-cores 30 may allow for inspection device 4 to transmit an electro-magnetic field 36 three hundred and sixty degrees, which may allow inspection device 4 to inspect the entirety of tube 12, surrounding tubes, and/or casing 14.

Figure 5A:
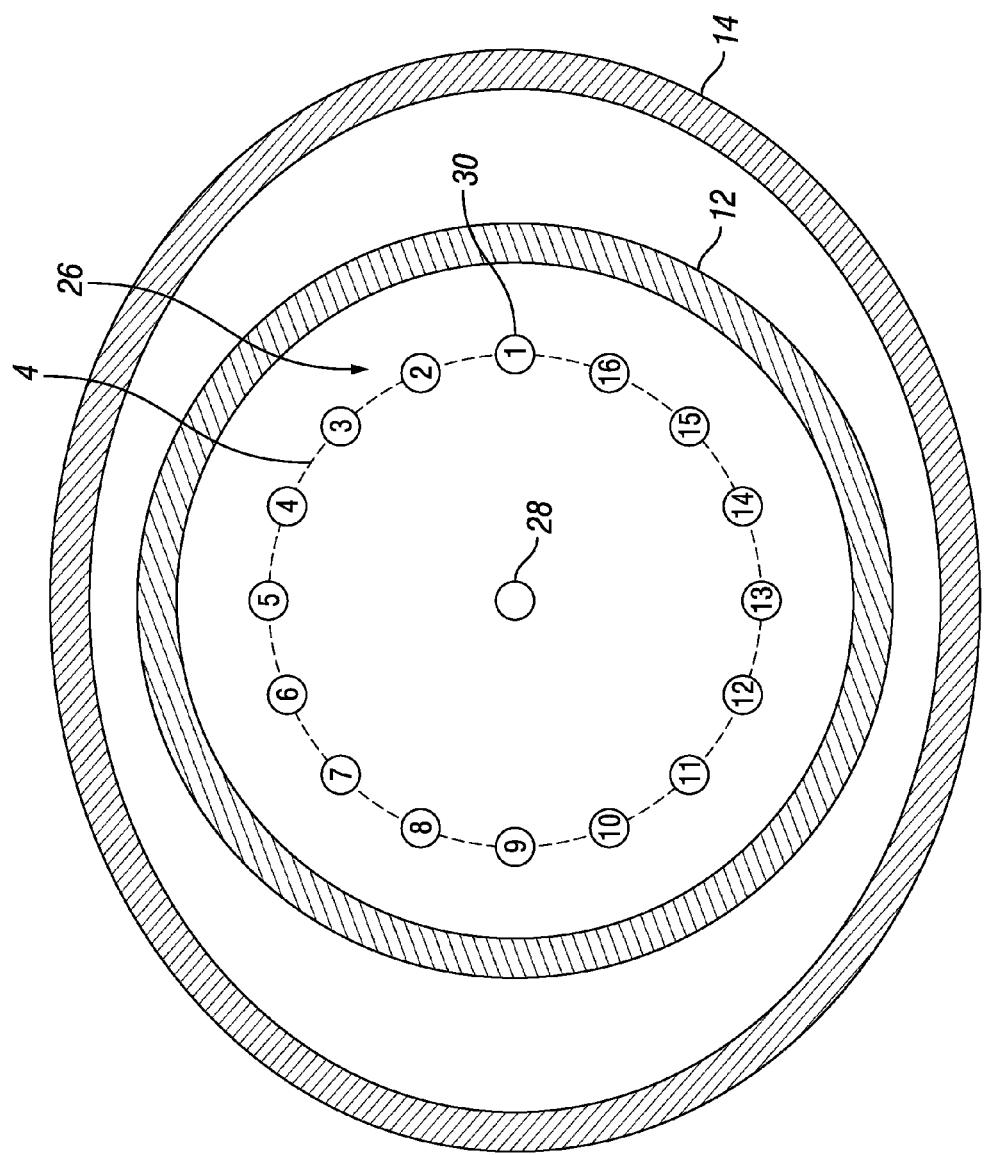
FIG. 5a illustrates an embodiment of a deformation casing.
Figure 5B:
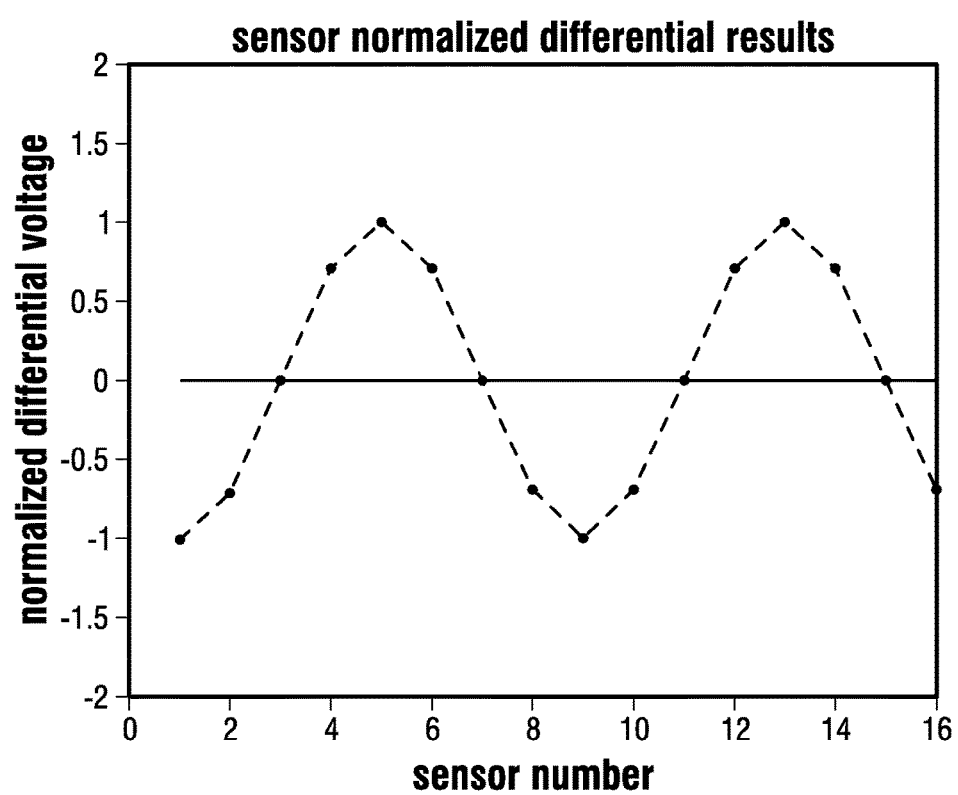
FIG. 5b illustrates a graph illustrating the detection of a deformation casing.

As illustrated in FIGS. 5a and 5b, inspection device 4 may traverse through a casing 14 which may be deformed. Sensor array 26 may transmit an electro-magnetic field which may be used to identify a deformed casing 14. In embodiments, peripheral ferri-cores 30 may transmit the electro-magnetic field three hundred and sixty degrees, which may induce an eddy current in tubing 12 and casing 14. Center receiver coil 28 may sense and record the voltage produced by the transmission of the electro-magnetic field, which may serve as a base to compare against voltages sensed by peripheral receivers 32. FIG. 5b illustrates an example of the voltage recorded by each peripheral receiver 32. In embodiments, peripheral receivers 32, identified as marker 1 and marker 9, may sense a voltage less than the voltage sensed by center receiver coil 28. The small amount of voltage sensed may indicate that the casing 14 wall may be farther away than expected. Marker 5 and marker 13 may sense a voltage that may be higher than the base voltage sensed by center receiver coil 28. A large amount of voltage may indicate that the casing wall may be closer than expected. The graph shown in FIG. 5b may indicate that casing 14 is deformed from the pressure exerted upon it by an underground formation. Sensor array 26 may further be able to sense a non-centered tubing 12 in casing 14.

Figure 6A:
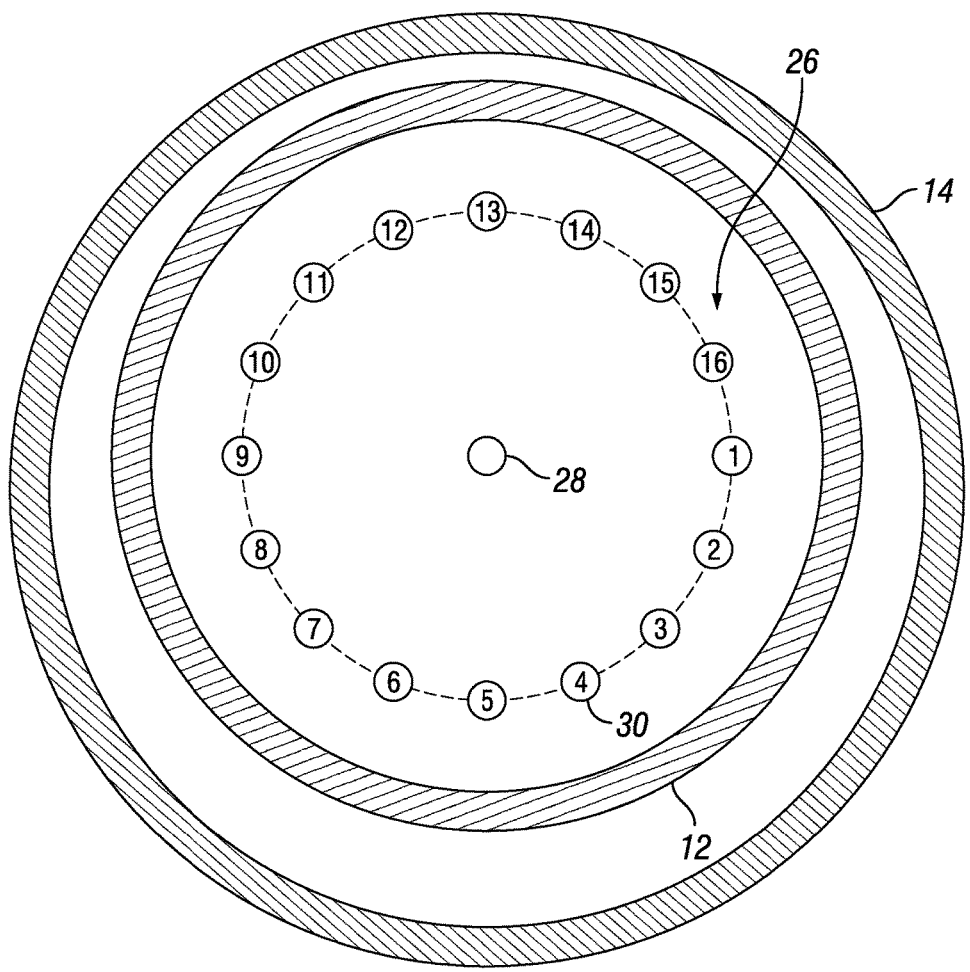
FIG. 6a illustrates an embodiment of a non-centered casing.
Figure 6B:
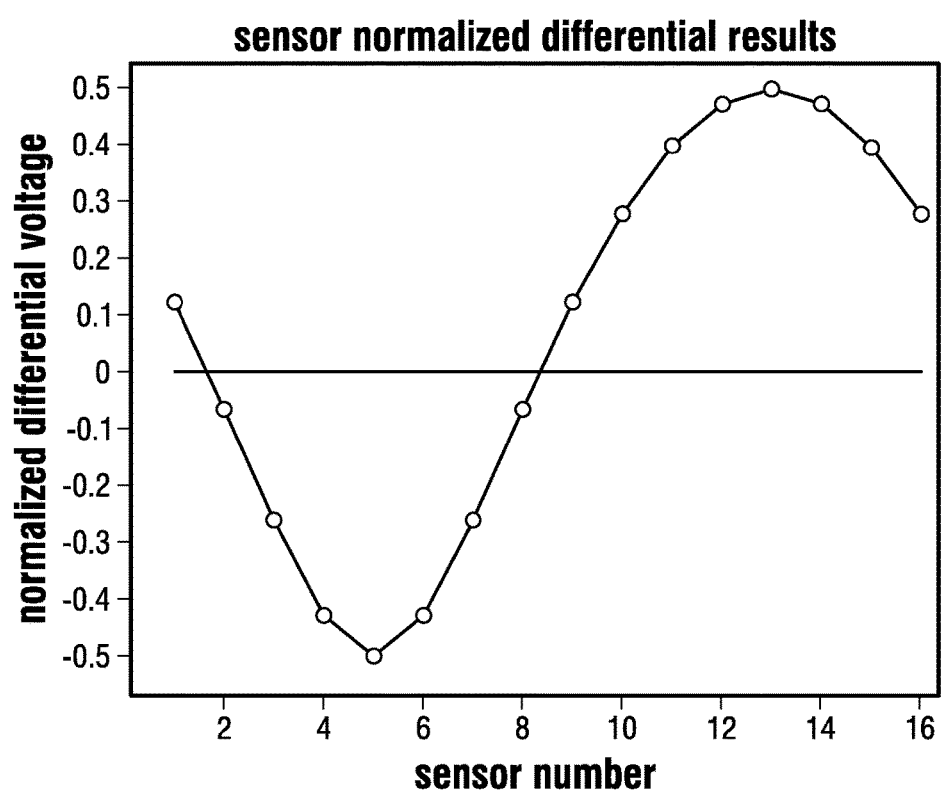
FIG. 6b is a graph illustrating the detection of a non-centered casing.

FIGS. 6a and 6b illustrate when tubing 12 may not be centered in casing 14. Sensor array 26 may transmit an electro-magnetic field which may help to identify when tubing 12 may not be centered in casing 14. In embodiments, peripheral ferri-cores 30 may transmit the electro-magnetic field three hundred and sixty degrees, which may induce an eddy current in tubing 12 and casing 14. Center receiver coil 28 may sense and record the voltage produced by the transmission of the electro-magnetic field, which may serve as a base to compare against voltages sensed by peripheral receivers 32. FIG. 6b illustrates an example of the voltage recorded by each peripheral receiver 32. In embodiments, peripheral receivers 32, identified as marker 5, may sense a voltage less than the base voltage sensed by center receiver coil 28. The small amount of voltage sensed may indicate that the casing 14 wall may be farther away than expected. Marker 13 may sense a voltage that may be higher than the voltage sensed by center receiver coil 28. A large amount of voltage may indicate that the casing wall may be closer than expected. The graph shown in FIG. 6b may indicated that tubing 12 may not be centered in casing 14. Sensor array 26 may further be able to detect sections of tubing 12 that may be thinner than other areas of tubing 12.

Figure 7A:
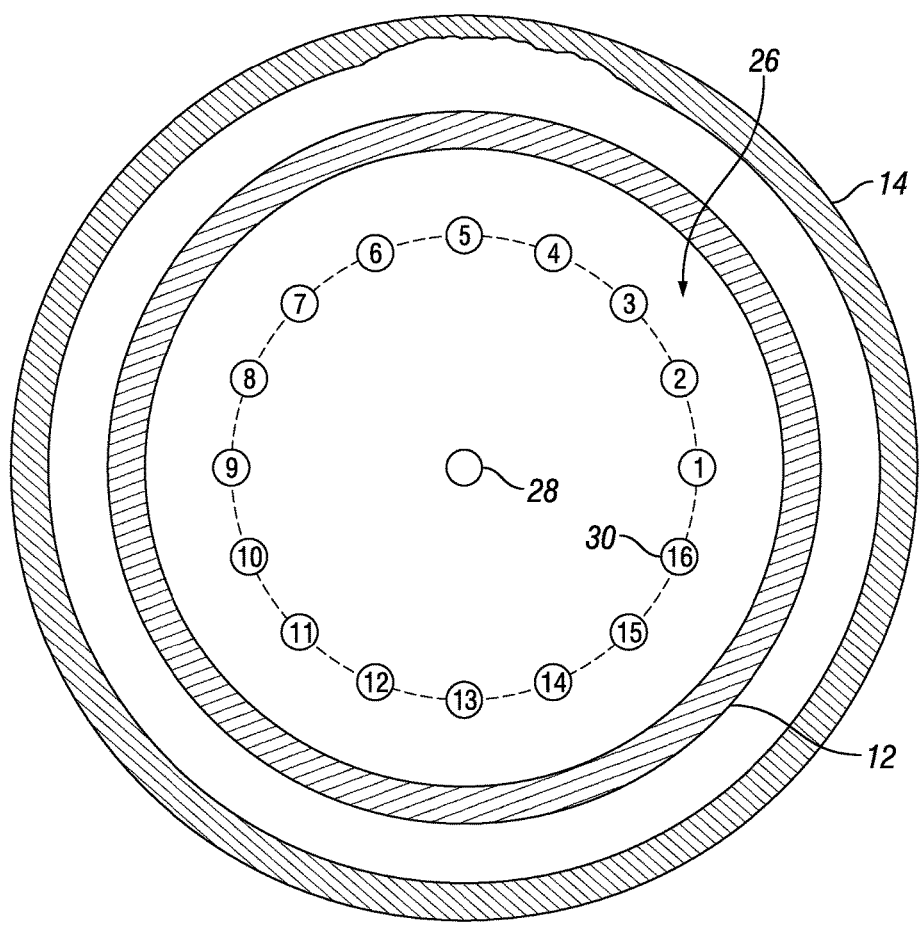
FIG. 7a illustrates an embodiment of a defect within a casing.
Figure 7B:
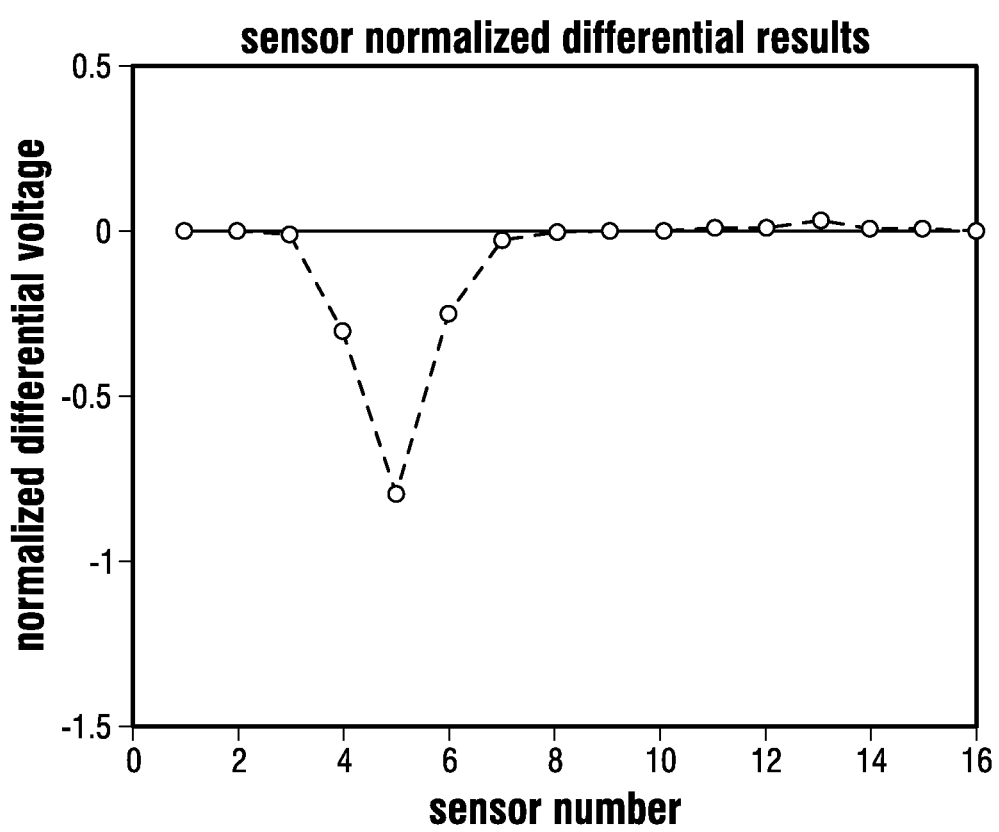
FIG. 7b is a graph illustrating the detection of a defect within a casing.

Casing 14, as illustrated in FIGS. 7a and 7b, may have a segment of a casing 14 wall that may be thinner than other segments of a casing 14 wall. Sensor array 26 may transmit an electro-magnetic field which may help to identify thinner segments of the casing 14 wall. In embodiments, peripheral ferri-cores 30 may transmit the electro-magnetic field three hundred and sixty degrees, which may induce an eddy current in tubing 12 and casing 14. Center receiver coil 28 may sense and record the voltage produced by the transmission of the electro-magnetic field. This may serve as a base to compare against voltages sensed by peripheral receivers 32. Graph 7b may illustrate the voltage recorded by each peripheral receiver 32. In embodiments, peripheral receivers 32, identified as marker 5, may sense a voltage less than the voltage sensed by center receiver coil 28. The small amount of voltage sensed may indicate that the casing 14 wall may be farther away than expected, which may indicate that the casing 14 wall may be thinner in this segment of the casing walls than other segments. Sensor array 26 may further be able to detect metal clamps 40 which may be attached to the outside of tubing 12 as shown in FIG. 8a.

Figure 8A:
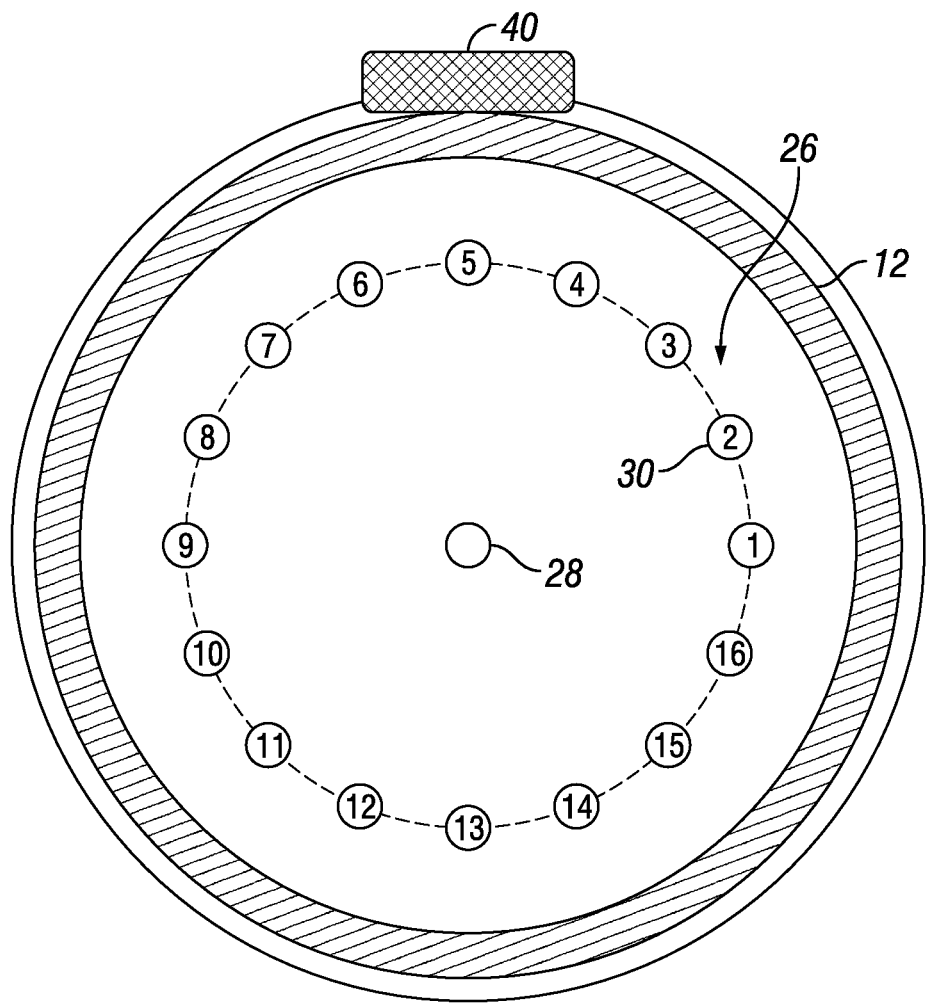
FIG. 8a illustrates an embodiment of a production monitoring system clip on a casing.
Figure 8B:
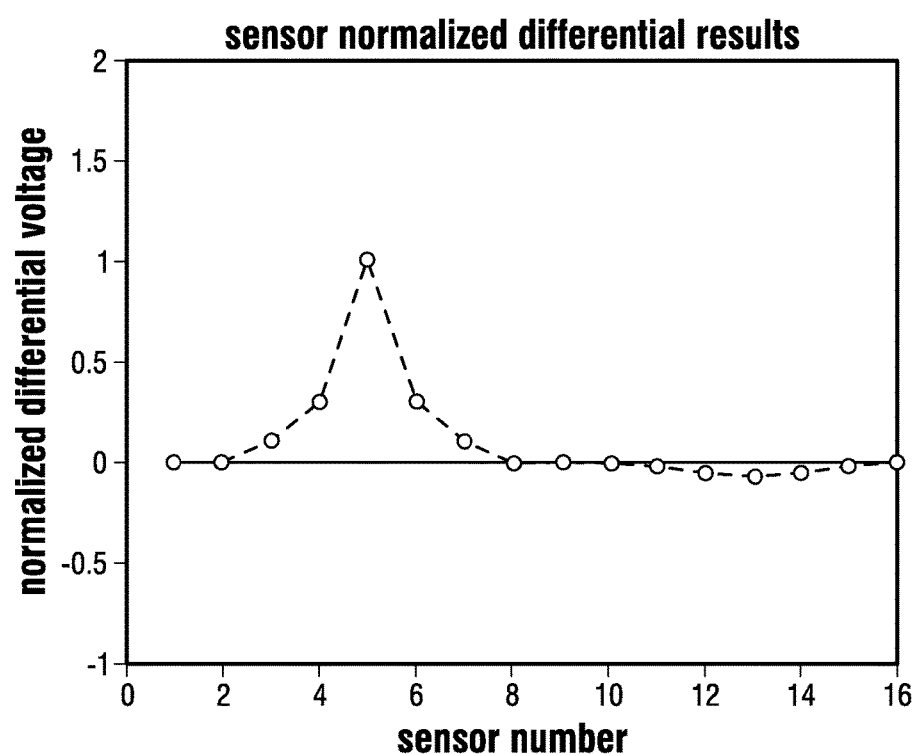
FIG. 8b is a graph illustrating the detection of a production monitoring system clip on a casing.

As illustrated in FIGS. 8a and 8b, sensor array 26 may be used to detect metal clips 40. Metal clips 40 may be used to hold a production monitoring system, not illustrated, in place. A production monitoring system may be a string of cables, specifically fiber optic cables, which may be used to sense the activity within tubing 12. The production monitoring system may wrap around tubing 12 during installation. For instance, oil companies may want to know the location of the production monitoring system to keep from harming the system when activities such as perforation of tube 12 and casing 13 may be performed. Locating metal clips 40 may indicate to an operator where the production monitoring system may be disposed. Sensor array 26 may transmit an electro-magnetic field which may help to identify metal clip 40 disposed outside tubing 12. In embodiments, peripheral ferri-cores 30 may transmit the electro-magnetic field three hundred and sixty degrees, which may induce an eddy current in tubing 12 and casing 14. Center receiver coil 28 may sense and record the voltage produced by the transmission of the electro-magnetic field. This may serve as a base to compare against voltages sensed by peripheral receivers 32. FIG. 8b may illustrate the voltage recorded by each peripheral receiver 32. In embodiments, peripheral receivers 32, identified as marker 5, may sense a voltage higher than the voltage sensed by center receiver coil 28. A higher amount of voltage sensed may indicate that the tubing wall may be closer than expected or may indicate the presence or a metal clip 40. Distinguishing between the two circumstances may be done by observing the pattern within the graph. A rolling graph, as illustrated in FIG. 8b may indicate that the tubing wall is closer than expected. A sharp spike in the graph may indicate that metal clip 40 may be attached to tubing 12.

Although the present invention and its advantages have been described in detail, it should be understood that various changes, substitutions and alterations may be made herein without departing from the spirit and scope of the invention as defined by the appended claims.

What is claimed is:

1. An inspection device comprising:
   a sensor array, wherein the sensor array comprises a center receiver coil, a ferri-core, a peripheral receiver, and a transmitter coil, wherein the peripheral receiver is wound around a portion of the ferri-core, wherein the transmitter coil is wound around a portion of the ferri-core, and wherein the ferri-core is held to the center receiver coil by the transmitter coil;
   a memory module; and
   a differential amplifier.

2. The inspection device of claim 1, wherein the memory module is a flash drive.

3. The inspection device of claim 1, wherein the sensor array is disposed within a non-ferrous sensor array housing.

4. The inspection device of claim 3, wherein the sensor array is disposed within a liquid medium within the sensor array housing.

* * * * *